(12) United States Patent
Tessien (10) Patent No.: US 7,922,793 B2
(45) Date of Patent: Apr. 12, 2011

(54) CAVITATION CHAMBER DEGASSING SYSTEM

(75) Inventor: Ross Alan Tessien, Nevada City, CA (US)

(73) Assignee: Impulse Devices, Inc., Grass Valley, CA (US)

( * ) Notice: Subject to any disclaimer, the term of this patent is extended or adjusted under 35 U.S.C. 154(b) by 1095 days.

(21) Appl. No.: 11/244,753

(22) Filed: Oct. 6, 2005

(65) Prior Publication Data

US 2007/0248471 A1    Oct. 25, 2007

Related U.S. Application Data

(63) Continuation-in-part of application No. 11/226,641, filed on Sep. 14, 2005.

(51) Int. Cl.
*B01F 11/00* (2006.01)

(52) U.S. Cl. .............................. 95/249; 95/250

(58) Field of Classification Search ........... 95/249, 95/250; 202/161
See application file for complete search history.

(56) References Cited

U.S. PATENT DOCUMENTS

| | | | |
|---|---|---|---|
| 3,853,500 A * | 12/1974 | Gassmann et al. ........ | 95/30 |
| 4,333,796 A | 6/1982 | Flynn | |
| 4,398,925 A * | 8/1983 | Trinh et al. ............ | 95/30 |
| 4,563,341 A | 1/1986 | Flynn | |
| 5,659,173 A | 8/1997 | Putterman et al. | |
| 5,858,104 A | 1/1999 | Clark | |
| 5,968,323 A | 10/1999 | Pless | |
| 6,361,747 B1 | 3/2002 | Dion et al. | |
| 6,500,239 B2 * | 12/2002 | Castellano et al. ....... | 95/247 |
| 2002/0090047 A1 | 7/2002 | Stringham | |

FOREIGN PATENT DOCUMENTS

| | | |
|---|---|---|
| WO | PCT/US95/15972 | 7/1996 |
| WO | PCT/US02/16761 | 12/2002 |
| WO | PCT/CA03/00342 | 9/2003 |

OTHER PUBLICATIONS

Blake et al, Acoustic Cavitation:The Fluid Dynamics of Non-Spherical Bubbles, Phil. Trans. R. Soc. Lond. A, 1999, pp. 251-267, vol. 357, Publisher: The Royal Society, Published in: Great Britain.

M. Dan et al., Ambient Pressure Effect on Single-Bubble Sonoluminescence, Physical Review Letters, Aug. 30, 1999, pp. 1870-1873, vol. 83, No. 9, Publisher: The American Physical Society, Published in: US.

(Continued)

*Primary Examiner* — David L Sorkin (74) *Attorney, Agent, or Firm* — C. Brandon Browning; Maynard Cooper & Gale, PC (57) ABSTRACT

A system and method for degassing a cavitation fluid is provided. The cavitation system of the invention includes a cavitation chamber with one or more cavitation drivers and a degassing system coupled to the chamber. One or more heaters, such as resistive heaters, are coupled to an external surface of the cavitation chamber such that heat from the heaters is transmitted through the wall of the cavitation chamber and into localized regions of the cavitation fluid contained within the cavitation chamber. The heater or heaters increase the temperature of the localized regions of the cavitation fluid to a temperature above the boiling temperature of the cavitation fluid, thereby creating vapor bubbles which capture gas trapped within the cavitation fluid through a rectified diffusion process. A cavitation fluid cooler can be used to insure that the average temperature of the cavitation fluid is below that of the boiling temperature.

11 Claims, 6 Drawing Sheets

OTHER PUBLICATIONS

Moss et al., Computed Optical Emissions from a Sonoluminescing Bubble, Physical Review E, Mar. 1999, pp. 2986-2992, vol. 59, No. 3, Published in: US.

Y.T. Didenko et al., Effect of Noble Gases on Sonoluminescence Temperatures during Multibubble Cavitation, Physical Review Letters, Jan. 24, 2000, pp. 777-780, vol. 84, No. 4, Publisher: The American Physical Society, Published in: US.

Gaitan et al, Experimental Observations of Bubble Response and Light Intensity Near the Threshold for Single Bubble Sonoluminescence, Physical Review E, May 1999, pp. 5495-5502, vol. 59, No. 5, Published in: US.

Barber et al, Sensitivity of Sonoluminescence to Experimental Parameters, Physical Review Letters, Feb. 28, 1994, pp. 1380-1382, vol. 72, No. 9.

F.R. Young, Sonoluminescence from Water Containing Dissolved Gases, J. Acoust. Soc. Am., Jul. 1996, pp. 100-104, vol. 60, No. 1, Publisher: Acoustical Society of America, Published in: US.

Putterman, Sonoluminescence:Sound Into Light, Scientific American, Feb. 1995, pp. 46-51.

Gaitan et al, Sonoluminescence and Bubble Dynamics for a Single, Stable, Cavitation Bubble, J. Acoust. Soc. Am., Jun. 1992, pp. 3166-3183, vol. 91, No. 6, Publisher: Acoustical Society of America.

Crum, Sonoluminescence, Physics Today, Sep. 1994, pp. 22-29, Publisher: American Institute of Physics, Published in: US.

Bollinger, Ultra Cavitation, http://wiretap.area.com/Gopher/Library/Article/Sci/cavitate.ult, Sep. 17, 2001, pp. 1-26.

\* cited by examiner

CAVITATION CHAMBER DEGASSING SYSTEM

CROSS-REFERENCES TO RELATED APPLICATIONS

This application is a continuation-in-part of U.S. patent application Ser. No. 11/226,641 filed Sep. 14, 2005, the disclosure of which is incorporated herein by reference for any and all purposes.

FIELD OF THE INVENTION

The present invention relates generally to cavitation processes and, more particularly, to a method and apparatus for degassing a cavitation system.

BACKGROUND OF THE INVENTION

Sonoluminescence is a well-known phenomena discovered in the 1930's in which light is generated when a liquid is cavitated. Although a variety of techniques for cavitating the liquid are known (e.g., spark discharge, laser pulse, flowing the liquid through a Venturi tube), one of the most common techniques is through the application of high intensity sound waves.

In essence, the cavitation process consists of three stages; bubble formation, growth and subsequent collapse. The bubble or bubbles cavitated during this process absorb the applied energy, for example sound energy, and then release the energy in the form of light emission during an extremely brief period of time. The intensity of the generated light depends on a variety of factors including the physical properties of the liquid (e.g., density, surface tension, vapor pressure, chemical structure, temperature, hydrostatic pressure, etc.) and the applied energy (e.g., sound wave amplitude, sound wave frequency, etc.).

It is generally recognized that during the collapse of a cavitating bubble extremely high temperature plasmas are developed, leading to the observed sonoluminescence effect. This phenomena is at the heart of a considerable amount of research as scientists and engineers attempt to both completely characterize the phenomena and find applications for it. Noted applications include sonochemistry, chemical detoxification, ultrasonic cleaning and nuclear fusion.

U.S. Pat. No. 4,333,796 discloses a cavitation chamber comprised of a refractory metal such as tungsten, titanium, molybdenum, rhenium or some alloy thereof. Acoustic energy is supplied to the liquid (e.g., lithium or an alloy thereof) within the chamber by six metal acoustic horns coupled to transducers. The tips of the horns project into the chamber while the rearward portion of each horn is coupled to a heat exchange system, the heat exchange system withdrawing heat generated by the reactions within the chamber. In one disclosed embodiment, the source (i.e., deuterium) is introduced into the cavitation medium through a conduit attached to the top of the chamber, the concentration of the source being controlled by the dissociation pressure over the surface of the host liquid. In an alternate disclosed embodiment, an external processing system with a combination pump and mixer removes deuterium and tritium gases released from the cavitation zone and trapped within the chamber or tritium gases trapped within the Li-blanket surrounding the chamber and then reintroduces the previously trapped deuterium and tritium into the cavitation zone via a conduit coupled to the cavitation chamber. Additional deuterium may also be introduced into the mixer.

U.S. Pat. No. 4,563,341, a continuation-in-part of U.S. Pat. No. 4,333,796, discloses a slightly modified, cylindrical cavitation chamber. The chamber is surrounded by an external heating coil which allows the liquid within the chamber to be maintained at the desired operating temperature. The system is degassed prior to operation by applying a vacuum through a duct running through the cover of the chamber. During operation, the inventor notes that graphite, dissolved in the host liquid metal, is converted to diamond. The diamond-rich host material is removed via an outlet duct adjacent to the bottom of the chamber and graphite-rich host material is removed via an outlet duct adjacent to the upper end of the chamber. Additional host material and graphite are added by lowering rods comprised of the host material and graphite, respectively, into the heated chamber.

U.S. Pat. No. 5,659,173 discloses a sonoluminescence system that uses a transparent spherical flask fabricated from Pyrex®, Kontes®, quartz or other suitable glass and ranging in size from 10 milliliters to 5 liters. The inventors disclose that preferably the liquid within the flask is degassed and the flask is sealed prior to operation. In one disclosed embodiment, the cavitation chamber is surrounded by a temperature control system, thus allowing the liquid within the chamber to be cooled to a temperature of 1° C.

PCT Application No. US02/16761 discloses a nuclear fusion reactor in which at least a portion of the liquid within the reactor is placed into a state of tension, this state of tension being less than the cavitation threshold of the liquid. The liquid preferably includes enriched deuterium or tritium, the inventors citing deuterated acetone as an exemplary liquid. In at least one disclosed embodiment, acoustic waves are used to pretension the liquid. In order to minimize the effects of gas cushioning during bubble implosion, the liquid is degassed prior to tensioning. After the desired state of tension is obtained, a cavitation initiation source, such as a neutron source, nucleates at least one bubble within the liquid, the bubble having a radius greater than a critical bubble radius. The nucleated bubbles are then imploded, the temperature generated by the implosion being sufficient to induce a nuclear fusion reaction.

PCT Application No. CA03/00342 discloses a nuclear fusion reactor in which a bubble of fusionable material is compressed using an acoustic pulse, the compression of the bubble providing the necessary energy to induce nuclear fusion. The nuclear fusion reactor is spherically shaped and filled with a liquid such as molten lithium or molten sodium. A pressure control system is used to maintain the liquid at the desired operating pressure. To form the desired acoustic pulse, a pneumatic-mechanical system is used in which a plurality of pistons associated with a plurality of air guns strike the outer surface of the reactor with sufficient force to form a shock wave within the liquid in the reactor. In one disclosed embodiment, the spherical reactor is coupled to a fluid flow circuit in which a pump and a valve control the flow of fluid. A reservoir containing a fusionable material, preferably in gaseous form, is in communication with the fluid flow circuit. When desired, a bubble of the fusionable material, preferably encapsulated in a spherical capsule, is released from the reservoir and into the fluid flow circuit, which then injects the bubble into a port at the bottom of the chamber.

Co-pending U.S. patent application Ser. No. 11/002,476, filed Dec. 1, 2004, discloses a multi-stage process for degassing cavitation fluid. During the first stage, the cavitation fluid contained within a separate reservoir is degassed using an attached vacuum system. During the second stage, the cavitation fluid is pumped into the cavitation chamber and cavitated. As a result of the cavitation process, gases dissolved within the cavitation fluid are released. The circulatory system provides a means of pumping the gases from the chamber and the vacuum system provides a means of periodically eliminating the gases from the system. As disclosed, the procedure could also use a third stage of degassing in which cavities are formed within the cavitation fluid within the chamber using any of a variety of means. Once formed, the cavities are cavitated, thereby releasing dissolved gases within the fluid which can then be removed using the circulatory system and the attached vacuum system.

A variety of sonoluminescence systems have been designed which typically require degassing. The present invention provides a method and apparatus for efficiently achieving such degassing in a cavitation system.

SUMMARY OF THE INVENTION

The present invention provides a system and method for degassing a cavitation fluid. The cavitation system of the invention includes a cavitation chamber with one or more cavitation drivers and a degassing system coupled to the chamber. One or more heaters, such as resistive heaters, are coupled to an external surface of the cavitation chamber such that heat from the heaters is transmitted through the wall of the cavitation chamber and into localized regions of the cavitation fluid contained within the cavitation chamber. The heater or heaters increase the temperature of the localized regions of the cavitation fluid to a temperature above the boiling temperature of the cavitation fluid without increasing the average temperature of the cavitation fluid to above the fluid's boiling temperature. In another aspect of the invention, a cavitation fluid cooler is used to maintain the average temperature of the cavitation fluid to below that of the boiling temperature. The cavitation fluid cooler is preferably used throughout the degassing process and may be used throughout the cavitation process itself. One suitable cooler is a refrigerated chamber which surrounds a portion of, or all of, the cavitation chamber. Alternately coolers can use cooling coils wrapped around at least a portion of the cavitation chamber.

In another embodiment of the invention, a method of degassing a cavitation fluid is provided. In accordance with this embodiment, localized regions within the cavitation fluid are heated to a temperature above the boiling temperature of the fluid, the heat being provided by one or more heaters thermally coupled to an external surface of the cavitation chamber. As a result of localized boiling, vapor bubbles are created which capture gas trapped within the cavitation fluid through the process of rectified diffusion. The bubbles then float to the top surface of the cavitation fluid, transporting the trapped gases to the space above the cavitation fluid and thereby concentrating the gases within this space. The concentrated gas which is left behind can be periodically removed with the system's vacuum pump. The localized heaters can be used immediately upon initiation of the degassing process, or after completion of a preliminary phase of degassing. In at least one embodiment, the heaters are used in conjunction with a cooler that maintains the average temperature of the cavitation fluid within the chamber to a temperature that is below that of the fluid's boiling temperature. The use of a cooler insures that only small localized areas of cavitation fluid boil and that the vapor bubbles formed by the heaters condense back to the liquid phase as they rise to the upper portion of the chamber.

A further understanding of the nature and advantages of the present invention may be realized by reference to the remaining portions of the specification and the drawings.

DESCRIPTION OF THE SPECIFIC EMBODIMENTS

Figure 1:
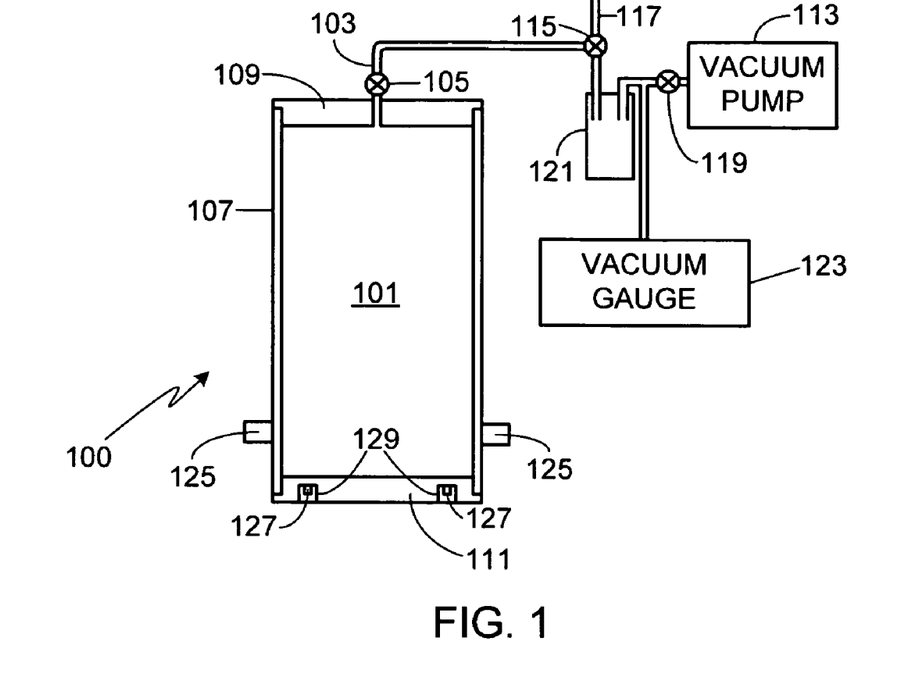
FIG. 1 is an illustration of an exemplary embodiment of the invention.

FIG. 1 is an illustration of an exemplary embodiment of the invention. System 100 includes a cavitation chamber 101 in which the desired cavitation processes, for example cavitation driven reactions, are performed. During system operation, chamber 101 can either be completely filled with cavitation fluid or partially filled with cavitation fluid, the latter approach leaving a cavitation fluid free surface within the chamber. If chamber 101 is completely filled, the system can still be run with a cavitation fluid free surface within coupling conduit 103. Alternately, chamber 101 can be completely filled and the chamber isolated from the system, for example with valve 105, such that there is not a free cavitation fluid surface during system operation.

In the embodiment illustrated in FIG. 1, chamber 101 is a cylindrical chamber. It should be appreciated, however, that chamber 101 can utilize other configurations. Particular configurations are typically selected to accommodate a specific cavitation process and its corresponding process parameters (e.g., cavitation fluid, pressure, temperature, reactants, etc.). Examples of other configurations include spherical chambers, hourglass-shaped chambers, conical chambers, cubical chambers, rectangular chambers, irregularly-shaped chambers, etc. An example of a cylindrical cavitation chamber is provided in co-pending U.S. patent application Ser. No. 11/038,344, filed Jan. 18, 2005, entitled *Fluid Rotation System for a Cavitation Chamber*, the entire disclosure of which is incorporated herein for any and all purposes. One method of fabricating a spherical chamber is described in detail in co-pending U.S. patent application Ser. No. 10/925,070, filed Aug. 23, 2004, entitled *Method of Fabricating a Spherical Cavitation Chamber*, the entire disclosure of which is incorporated herein for any and all purposes. Examples of hourglass-shaped chambers are provided in co-pending U.S. patent application Ser. No. 11/140,175, filed May 27, 2005, entitled *Hourglass-Shaped Cavitation Chamber*, and Ser. No. 11/149,791, filed Jun. 9, 2005, entitled *Hourglass-Shaped Cavitation Chamber with Spherical Lobes*, the entire disclosures of which are incorporated herein for any and all purposes.

Chamber 101 can be fabricated from any of a variety of materials, or any combination of materials. The primary considerations for material selection are the desired operating pressure and temperature of the chamber and system. Additionally, the chamber materials can be selected to simplify viewing of the sonoluminescence phenomena, for example utilizing a transparent material such as glass, borosilicate glass, or quartz glass (e.g., Pyrex®). Alternately chamber 101 can be fabricated from a more robust material (e.g., 17-4 precipitation hardened stainless steel) and one which is preferably machinable, thus simplifying fabrication. Alternately a portion of the chamber can be fabricated from one material while other portions of the chamber can be fabricated from one or more different materials. For example, in the preferred embodiment illustrated in FIG. 1, cylindrical portion 107 is fabricated from a transparent material (e.g., glass) while end caps 109 and 111 are fabricated from a metal (e.g., aluminum). In addition to the above considerations, preferably the material or materials selected for chamber 101 are relatively corrosion resistant to the intended cavitation fluid, thus allowing the chamber to be used repeatedly.

The selected dimensions of chamber 101 depend on many factors, including the cost of the cavitation fluid, chamber fabrication issues, operating temperature and frequency, sound speed, and the cavitation driver capabilities. In general, small chambers are preferred for situations in which it is desirable to limit the amount of the cavitation medium or in which driver input energy is limited while large chambers (e.g., 10 inches or greater) are preferred as a means of simplifying experimental set-up and event observation or when high energy reactions or large numbers of low energy reactions are being driven within the chamber. Thick chamber walls are preferred in order to accommodate high pressures.

In order to efficiently achieve high energy density (e.g., temperature) cavitation induced implosions within the cavitation fluid within chamber 101, preferably the cavitation fluid is first adequately degassed of unwanted contaminants. Without sufficient degassing, gas within the cavitation fluid will impede the cavitation process by decreasing the maximum rate of collapse as well as the peak stagnation pressure and temperature of the plasma within the cavitating bubbles. It will be understood that the term "gas", as used herein, refers to any of a variety of gases that are trapped within the cavitation fluid, these gases typically reflecting the gases contained within air (e.g., oxygen, nitrogen, argon, etc.). In contrast, "vapor" only refers to molecules of the cavitation fluid that are in the gaseous phase.

Degassing is preferably performed with a vacuum pump 113 that is coupled to chamber 101 via conduit 103. It will be understood that the degassing techniques of the present invention can also be utilized within a separate degassing reservoir in which the cavitation fluid is degassed prior to filling chamber 101. In yet another alternate embodiment, the cavitation medium can be degassed initially outside of chamber 101 and then again within chamber 101.

In the embodiment illustrated in FIG. 1, a three-way valve 115 allows the system to be coupled to the ambient atmosphere via conduit 117 or to vacuum pump 113. It will be appreciated that three-way valve 115 can be replaced with a pair of two-way valves (not shown). Valve 119 provides a means for isolating the system from pump 113. Preferably a trap 121 is used to insure that cavitation fluid is not drawn into vacuum pump 113 or vacuum gauge 123. Preferably trap 121 is cooled so that any cavitation medium entering the trap condenses or solidifies. Vacuum gauge 123 is used to provide an accurate assessment of the system pressure. If the cavitation system becomes pressurized, prior to re-coupling the system to either vacuum gauge 123 or vacuum pump 113, the cavitation system pressure is bled down to an acceptable level using three-way valve 115.

A cavitation medium filling system, not shown, is coupled to chamber 101 and used to fill the chamber to the desired level. It will be appreciated that the operating level for chamber 101 is based on obtaining the most efficient cavitation action. For example, while a spherical chamber may be most efficiently operated when it is completely full, a vertically aligned cylindrical chamber (e.g., the chamber shown in FIG. 1) may operate most efficiently when it is not completely full, thus providing a free cavitation liquid surface at the top of the chamber. The filling system may utilize a simple fill tube (e.g., conduit 117), a separate fluid reservoir, or other filling means. Regardless of the method used to fill chamber 101, preferably the system is evacuated prior to filling, thus causing the cavitation medium to be drawn into the system (i.e., utilizing ambient air pressure to provide the pressure to fill the system).

Although not required, the filling system may include a circulatory system, such as that described in co-pending U.S. patent application Ser. No. 11/001,720, filed Dec. 1, 2004, entitled *Cavitation Fluid Circulatory System for a Cavitation Chamber*, the disclosure of which is incorporated herein for any and all purposes. Other components that may or may not be coupled to the cavitation medium filling and/or circulatory system include bubble traps, cavitation fluid filters, and heat exchange systems. Further descriptions of some of these variations are provided in co-pending U.S. patent application Ser. No. 10/961,353, filed Oct. 7, 2004, entitled *Heat Exchange System for a Cavitation Chamber*, the disclosure of which is incorporated herein for any and all purposes.

One or more drivers 125 are coupled to chamber 101, drivers 125 being used to drive the desired cavitation process within chamber 101. Clearly the invention is not limited to a specific number, type, mounting technique or mounting location for the driver(s). In the illustrated embodiment, driver 125 is a ring of piezoelectric material that is bonded, for example with an epoxy, to the outer circumference of chamber 101. Examples of other types of drivers suitable for use with a cavitation chamber and cavitation system utilizing the present invention are given in co-pending U.S. patent application Ser. No. 10/931,918, filed Sep. 1, 2004, entitled *Acoustic Driver Assembly for a Spherical Cavitation Chamber*; Ser. No. 11/123,388, filed May 5, 2005, entitled *Acoustic Driver Assembly With Recessed Head Mass Contact Surface*; Ser. No. 11/123,381, filed May 6, 2005, entitled *Acoustic Driver Assembly With Restricted Contact Area*; and Ser. No. 11/068,080, filed Feb. 28, 2005, entitled *Hydraulic Actuated Cavitation Chamber*, the disclosures of which are incorporated herein in their entirety for any and all purposes.

As previously described, prior to cavitating the fluid with the cavitation chamber, preferably the cavitation fluid is degassed, thus insuring high intensity vapor implosions. The amount of degassing that is required depends on the sensitivity of the reactants to the presence of dissolved gases and/or the requirements placed on the system for high stagnation temperature and pressure. If a high degree of degassing is required, some prior systems have employed a multi-step degassing procedure. In such an approach initial degassing is performed using a vacuum pump (e.g., vacuum pump 113). This step typically takes between 30 and 60 minutes, depending primarily upon the capacity of the vacuum pump, the volume of the cavitation chamber, and the vapor pressure of the cavitation fluid. After completion of the initial degassing, additional degassing can be performed using the chamber's cavitation drivers. During this step, the acoustic energy input into the chamber from the drivers tears cavities within the cavitation medium. As the newly formed cavities expand, gas from the fluid that remains after the initial degassing step enters into the cavities. During cavity collapse, however, not all of the gas re-enters the fluid. Accordingly a result of the cavitation process is the removal of dissolved gas from the cavitation fluid via rectified diffusion and the generation of bubbles.

Figure 2:
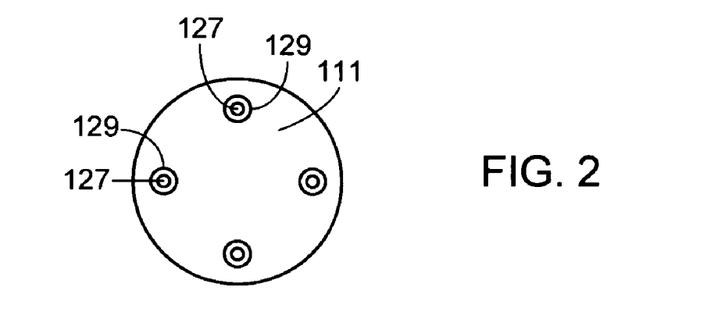
FIG. 2 is a bottom view of the lower end cap of the embodiment shown in FIG. 1.

Although cavitation is a viable approach to degassing the cavitation fluid, due to the violent cavitation that can occur before the cavitation fluid is sufficiently degassed, this approach may damage a fragile (e.g., glass) cavitation chamber. Accordingly the inventor has found that a better way to degas the cavitation fluid is to install one or more small, localized heaters within a wall(s) of the cavitation chamber. For example, in the embodiment illustrated in FIG. 1 multiple heaters 127 are mounted to an external surface of bottom end cap 111. FIG. 2 is an end view of end cap 111. Preferably heaters 127 are mounted within recesses bored, or otherwise fabricated, within end cap 111 as shown. Mounting heaters 127 within recesses is a preferred approach as it helps to localize the effects of the heaters by minimizing the separation between the heaters and the cavitation fluid within the chamber. Preferably heaters 127 are resistive heaters although it will be appreciated that other heat sources can be used with the invention.

Figure 3:
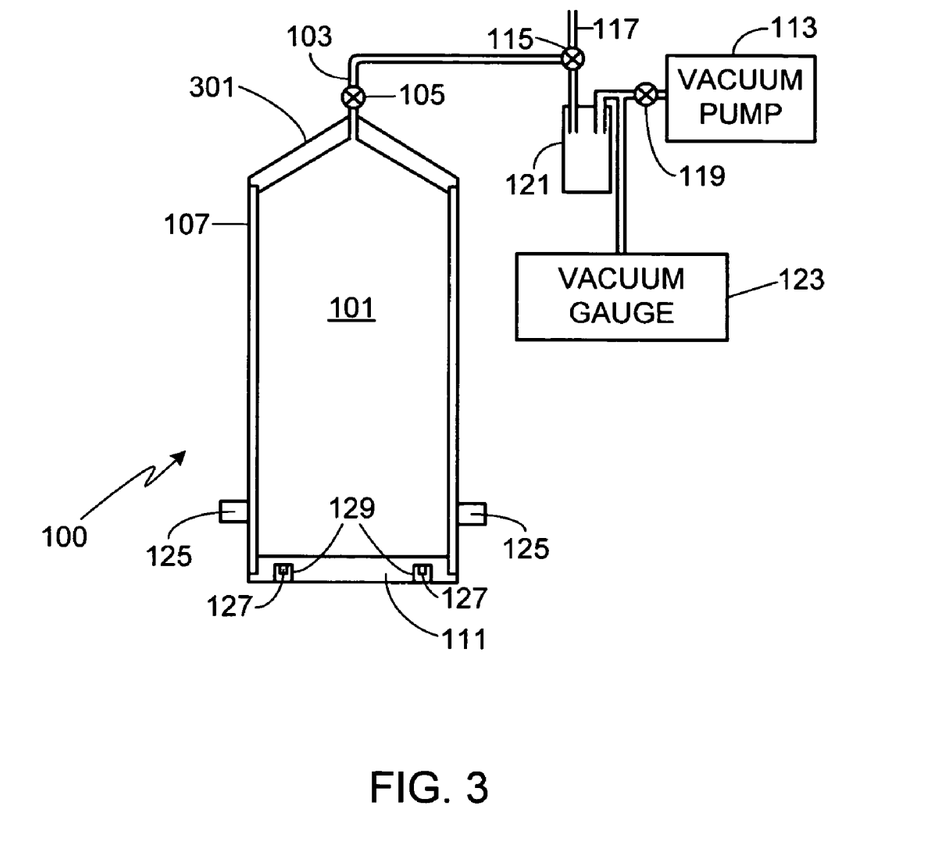
FIG. 3 is an illustration of a cavitation chamber similar to that shown in FIG. 1, except for the inclusion of a conically-shaped end cap designed to enhance gas removal.

In use, heaters 127 cause localized boiling of the cavitation fluid contained within the chamber, thus creating small vapor bubbles. As the vapor bubbles rise through the cavitation medium, gas trapped within the cavitation fluid passes into the bubbles through the process of rectified diffusion. The bubbles, due to their buoyancy, continue to drift to the top of the chamber where the gas can be removed, when desired, using vacuum pump 113. If desired, the top surface of chamber 101 can be shaped, for example conically-shaped as illustrated in FIG. 3 (e.g., surface 301), with conduit 103 coupled to the uppermost portion of the top surface. Shaping the top surface of chamber 101 helps to guide the bubbles out of the chamber and insure that the bubbles are not trapped within the chamber. Preferably heaters 127 are mounted at the lowermost portion of chamber 101 (e.g., bottom end cap 111), thus maximizing the distance traveled by the vapor bubbles and thus the degassing efficiency of the process.

As previously noted, the present invention is not limited to a specific chamber configuration, driver configuration, or a specific circulatory and/or fluid filling system. For example, system 400 shown in FIG. 4 utilizes a spherical chamber 401 with multiple drivers 403. A pair of conduits 405/407 couple chamber 401 to a reservoir 409, reservoir 409 preferably large enough to hold sufficient cavitation fluid to fill chamber 401. Reservoir 409, and thus chamber 401, is coupled to a vacuum pump 411 via three-way valve 413. Valve 413 also allows the system to be coupled to the ambient atmosphere via conduit 415. Vacuum gauge 417 is used to monitor the pressure within system 400. The circulatory system of this embodiment also includes at least one pump 419 and multiple coupling conduits 421-423 that can be used, in addition to conduit 415, to fill and/or drain the system.

Figure 4:
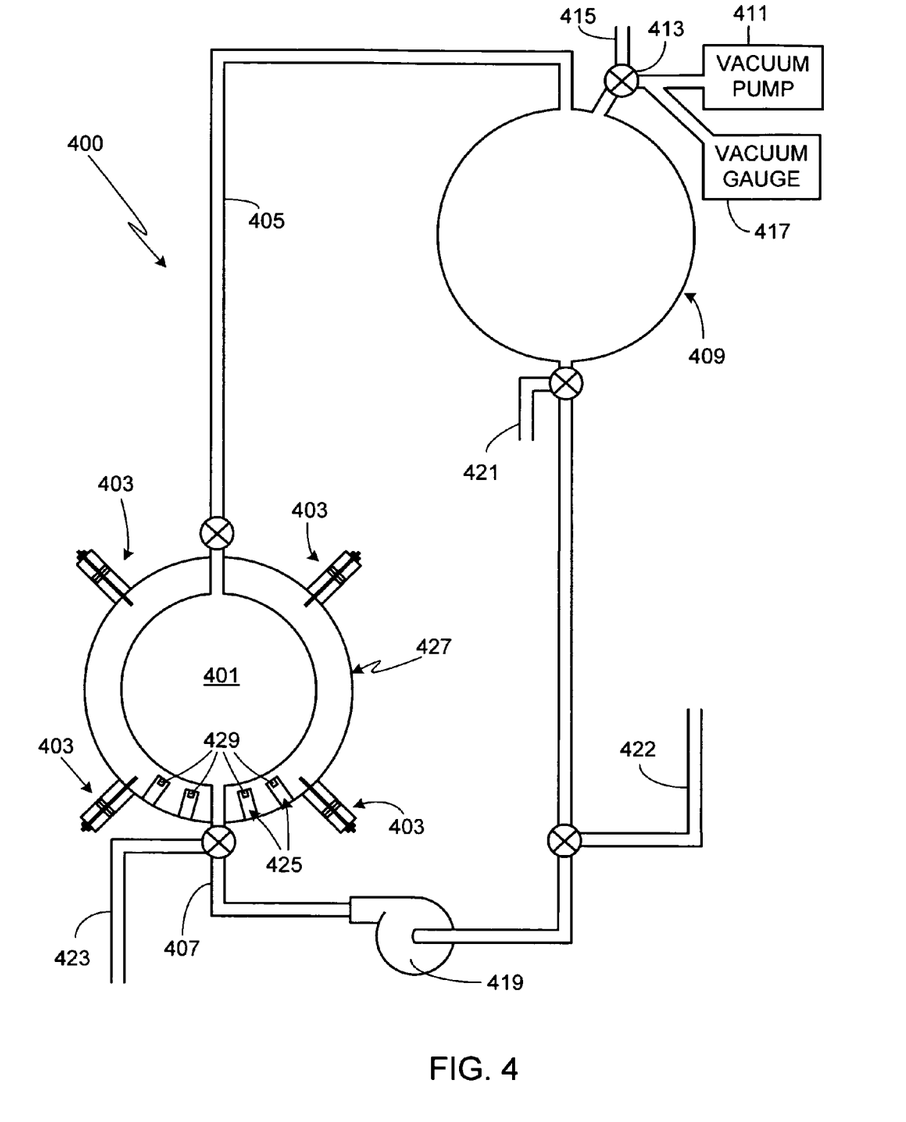
FIG. 4 is an illustration of an embodiment of the invention using a spherical cavitation chamber.

In this embodiment, multiple recesses 425 are bored into the outer surface 427 of chamber 401. Within each recess 425 is mounted a heat source 429 (e.g., resistive heater). Heat sources 429 are used to accelerate the degassing procedure, as previously disclosed. Although heaters 429 are preferably attached to the cavitation chamber, it will be appreciated that they can also be attached to reservoir 409 (not shown).

As described above, the heaters of the present invention (e.g., heaters 127, heaters 429) aid the degassing procedure by causing localized boiling of the cavitation fluid. The vapor bubbles created by the boiling process capture gas trapped within the cavitation fluid as they float to the top of the chamber. The vapor condenses back to the fluid phase, leaving the gas to be periodically removed with the system's vacuum pump (e.g., pump 113, pump 411). The localized heaters of the invention can be used immediately upon initiation of the degassing process, or after completion of a preliminary phase of degassing. It will be appreciated that the use of the localized heaters of the invention does not preclude the use of other degassing procedures such as low energy cavitation, neutron bombardment, etc.

Although the heaters described above can create the desired localized boiling of the cavitation fluid, the inventor has found that preferably the heaters are used in conjunction with a cooler that maintains the average temperature of the cavitation fluid within the chamber at a temperature below that of its boiling temperature. This approach insures that only small localized areas of cavitation fluid boil and that the vapor bubbles formed by the heaters condense back to the liquid phase as they rise to the upper portion of the chamber.

Figure 5:
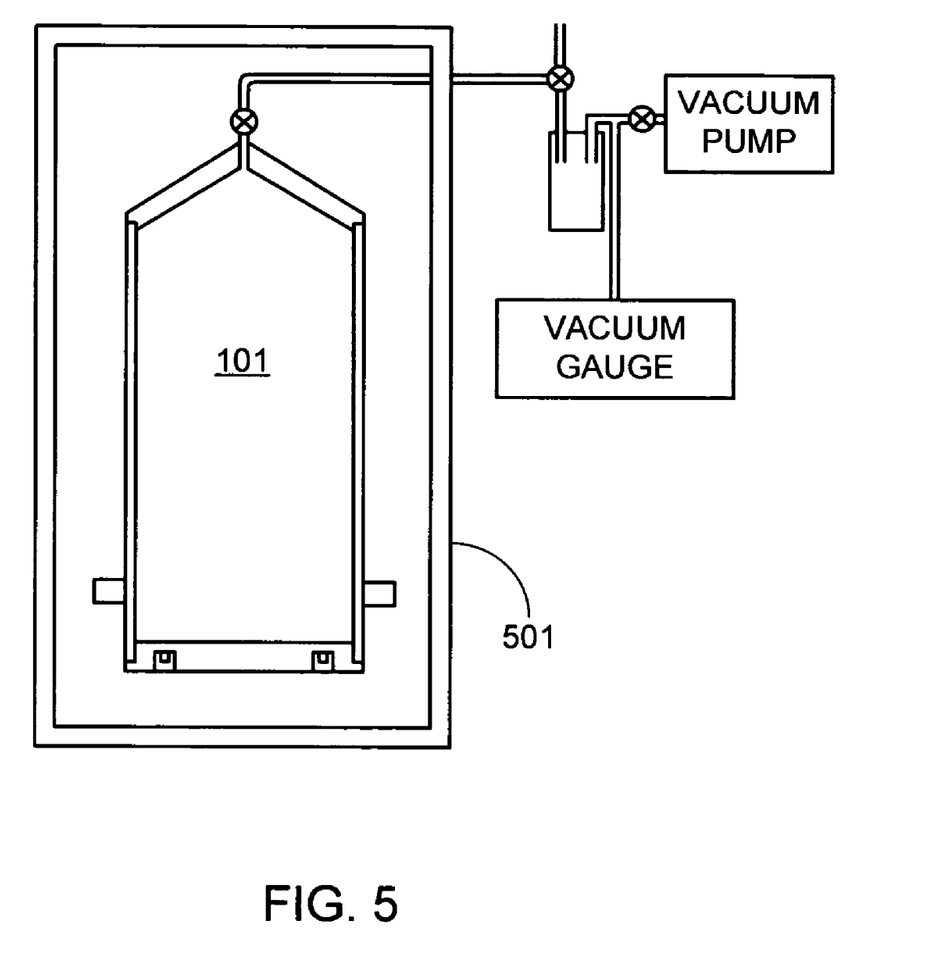
FIG. 5 is an illustration of a cavitation chamber similar to that shown in FIG. 3 housed within a cooling chamber.
Figure 6:
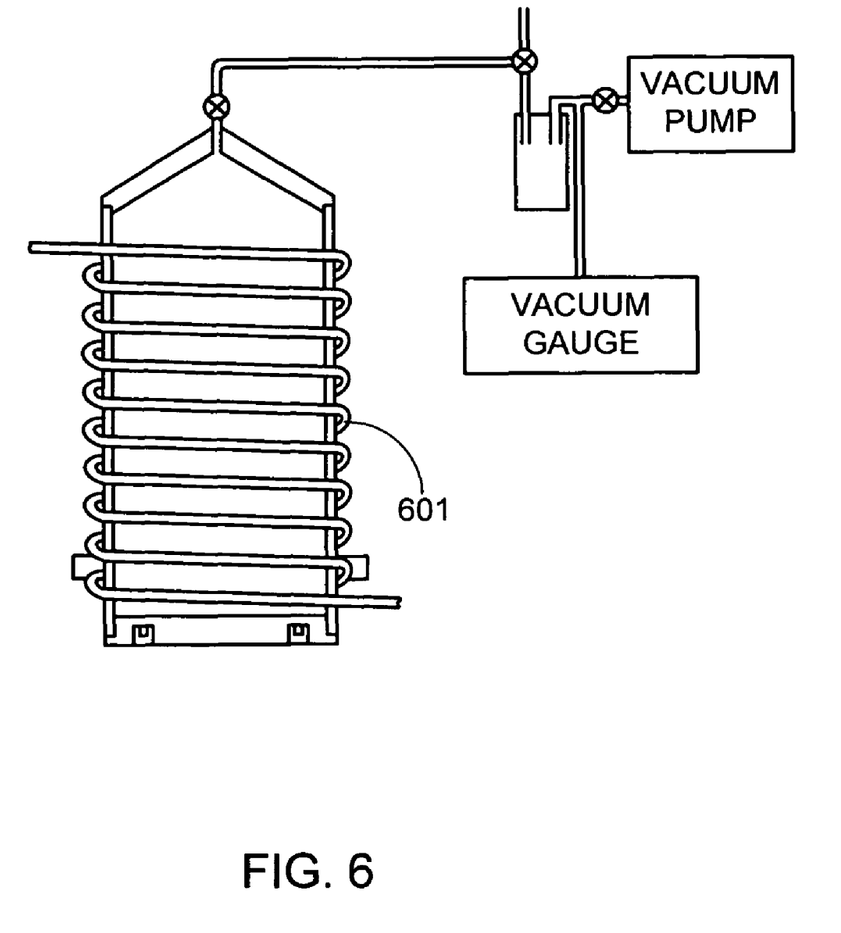
FIG. 6 is an illustration of a cavitation chamber similar to that shown in FIG. 3 wrapped with cooling coils.
Figure 7:
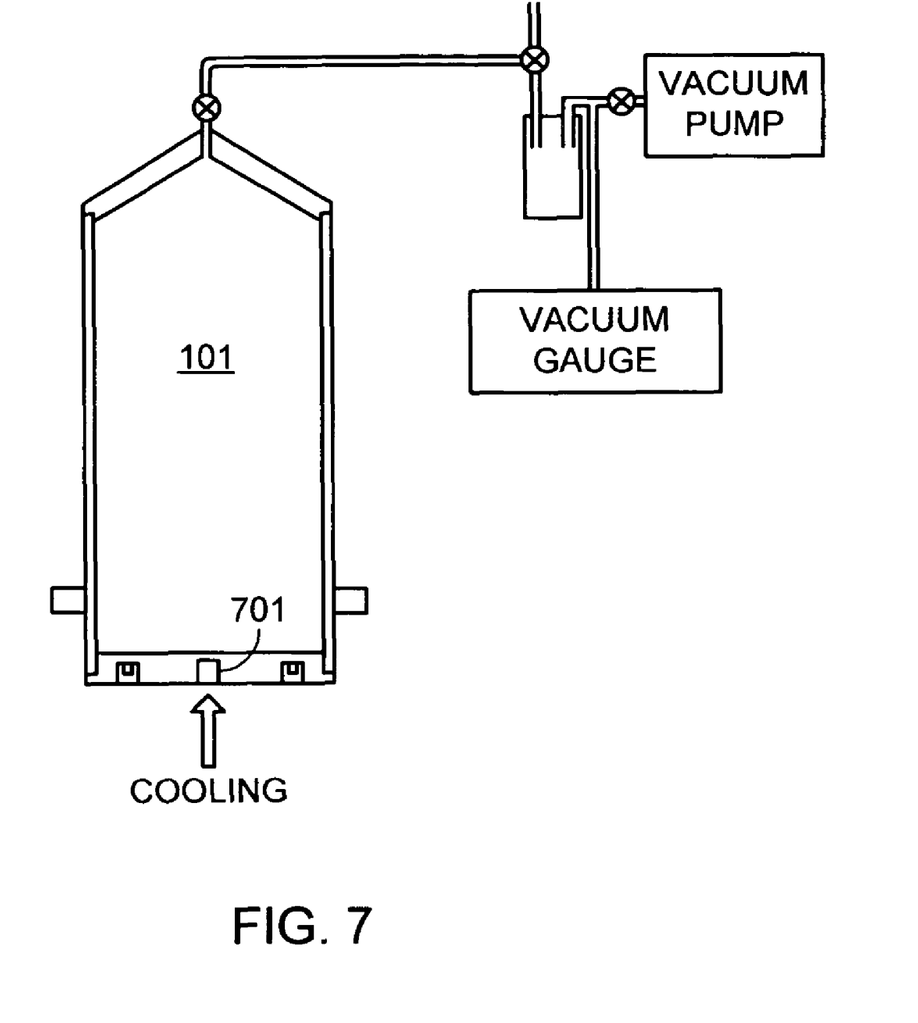
FIG. 7 is an illustration of a cavitation chamber similar to that shown in FIG. 3 utilizing a small area cooler.

FIGS. 5-7 illustrate preferred embodiments of the invention based on the configuration shown in FIG. 3, these embodiments including means for cooling the cavitation fluid to a temperature below the boiling point for the fluid. As illustrated in FIG. 5, chamber 101 is enclosed within a refrigerated chamber 501. As illustrated in FIG. 6, chamber 101 is wrapped with multiple cooling coils 601 that are coupled to a refrigeration system (not shown). As illustrated in FIG. 7, a small region 701, preferably in close proximity to the cavitation fluid (e.g., a bored recess) is subjected to cooling which then, in turn, cools the cavitation fluid to the desired temperature. Region 701 can be cooled using any of a variety of means such as cold air jets, thermoelectric coolers (TECs), etc. Alternately, a cold finger can be mounted to region 701, the cold finger being subjected to the desired cooling means (e.g., cold air jets, TECs, cooling coil, etc.). It will be appreciated that other cooling techniques can also be used with the invention as well as combinations of different cooling means (e.g., cold air jet and cooling chamber) and that cooling the cavitation fluid within the chamber is not limited to a particular chamber or driver configuration.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A method of preparing a cavitation fluid contained within a cavitation system for cavitation, the method comprising the steps of:
    filling a cavitation chamber within said cavitation system with a quantity of the cavitation fluid, said cavitation fluid having a boiling temperature;
    coupling at least one cavitation driver to an external surface of the cavitation chamber, wherein the cavitation driver does not extend into the cavitation chamber;
    sealing the cavitation chamber;
    evacuating said cavitation chamber;
    heating regions of an external surface of said cavitation chamber;
    transferring heat from said regions of said external surface heated by said heating step to corresponding regions of an internal surface of said cavitation chamber, wherein said corresponding regions of said internal surface are heated to a temperature above said boiling temperature; and boiling portions of the cavitation fluid in proximity to said corresponding regions of said internal surface of said cavitation chamber while said cavitation chamber is sealed.

2. The method of claim 1, wherein said boiling step further comprises the steps of: forming bubbles within the cavitation fluid; and capturing a portion of a gas dissolved within the cavitation fluid within said bubbles, wherein said bubbles float to a cavitation fluid free surface.

3. The method of claim 2, further comprising the step of periodically removing said captured portion of said gas from said cavitation chamber.

4. The method of claim 1, wherein said evacuating step is performed after said boiling step.

5. The method of claim 1, wherein said evacuating step is performed periodically after initiation of said boiling step.

6. A method of preparing a cavitation fluid contained within a cavitation system for cavitation, the method comprising the steps of:
   filling a cavitation chamber within said cavitation system with a quantity of the cavitation fluid, said cavitation fluid having a boiling temperature;
   sealing the cavitation system;
   evacuating said cavitation chamber;
   heating regions of an external surface of said cavitation chamber;
   transferring heat from said regions of said external surface heated by said heating step to corresponding regions of an internal surface of said cavitation chamber, wherein said corresponding regions of said internal surface are heated to a temperature above said boiling temperature; and
   boiling portions of the cavitation fluid in proximity to said corresponding regions of said internal surface of said cavitation chamber, wherein the cavitation fluid is maintained at an average temperature below said boiling temperature during said heating, heat transferring and boiling steps by cooling the cavitation fluid within the cavitation chamber during at least one of said heating step, said heat transferring step and said boiling step.

7. The method of claim 6, wherein said boiling step further comprises the steps of: forming bubbles within the cavitation fluid; and capturing a portion of a gas dissolved within the cavitation fluid within said bubbles, wherein said bubbles float to a cavitation fluid free surface.

8. The method of claim 7, further comprising the step of periodically removing said captured portion of said gas from said cavitation chamber.

9. The method of claim 6, wherein said evacuating step is performed after said boiling step.

10. The method of claim 6, wherein said evacuating step is performed periodically after initiation of said cooling and boiling steps.

11. The method of claim 6, wherein said cooling step occurs during said heating step, said heat transferring step and said boiling step.

* * * * *